United States Patent [19]

Biltonen et al.

[11] 4,255,961
[45] Mar. 17, 1981

[54] DIFFERENTIAL CALORIMETER BASED ON THE HEAT LEAK PRINCIPLE

[75] Inventors: Rodney L. Biltonen; Donald B. Mountcastle, both of Charlottesville, Va.; Jaak Suurkuust, Lund, Sweden

[73] Assignee: University of Va. Alumni Patents Foundation, Charlottesville, Va.

[21] Appl. No.: 952,155

[22] Filed: Oct. 17, 1978

[51] Int. Cl.³ ........................................... G01K 17/00
[52] U.S. Cl. .................................. 73/15 B; 73/190 R
[58] Field of Search ............................ 73/15 B, 190 R

[56] References Cited

U.S. PATENT DOCUMENTS

| | | | |
|---|---|---|---|
| 3,059,471 | 10/1962 | Calvet | 73/15 |
| 3,263,484 | 8/1966 | Watson et al. | 73/15 |
| 3,283,560 | 11/1966 | Harden et al. | 73/15 |
| 3,373,607 | 3/1968 | Schoenlaub | 73/190 |
| 3,572,084 | 3/1971 | May | 73/15 |
| 4,149,401 | 4/1979 | Hentze | 73/15 |

*Primary Examiner*—Herbert Goldstein
*Attorney, Agent, or Firm*—Oblon, Fisher, Spivak, McClelland & Maier

[57] ABSTRACT

A differential scanning calorimeter based on the heat leak principle having a reference measuring cell and a sample measuring cell symmetrically seated within a copper heat sink surrounded by an isothermal shield. Each measuring cell includes a cylindrical stainless steel ampoule which contains a test substance, a honeycombed aluminum cell frame which supports the ampoule, and a pair of thermopiles which are placed between the aluminum cell frame and the copper heat sink and which measure the temperature difference between the two. A plurality of resistive heating elements wired in series are applied to different sections of the heat sink and the isothermal shield, each heating element having a resistance respectively proportional to the heat capacity of the heat sink sections and the shield. A common current is then passed through the heating elements, thus producing a highly uniform positive temperature scan with a minimum of residual temperature gradients existing within the heat sink. The ampoules in the measuring cells are individually pressurizable whereby calorimetric data as a function of pressure can be obtained.

25 Claims, 11 Drawing Figures

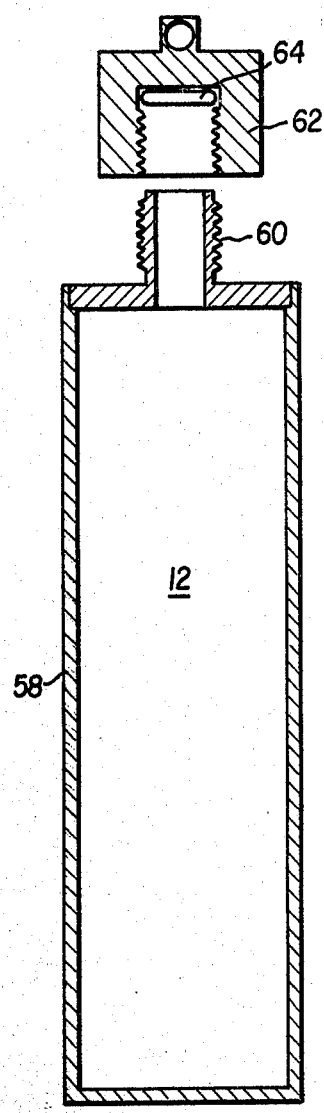
FIG.3a
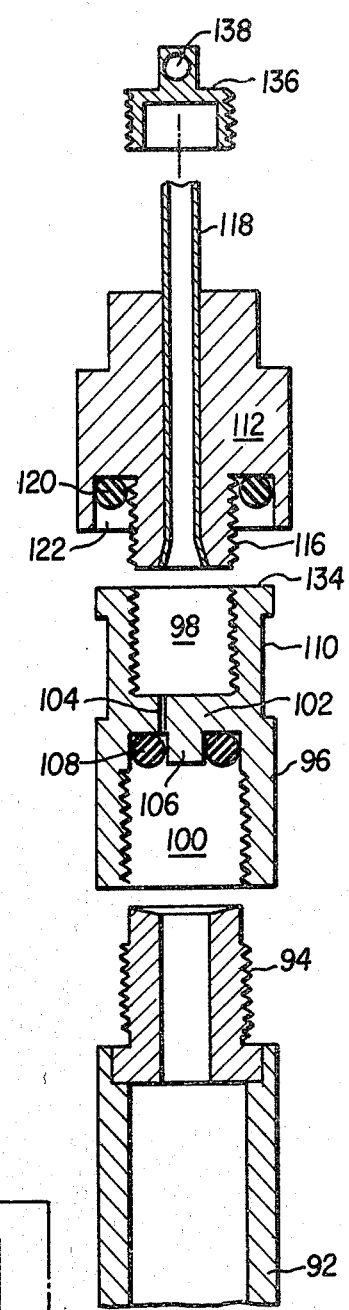
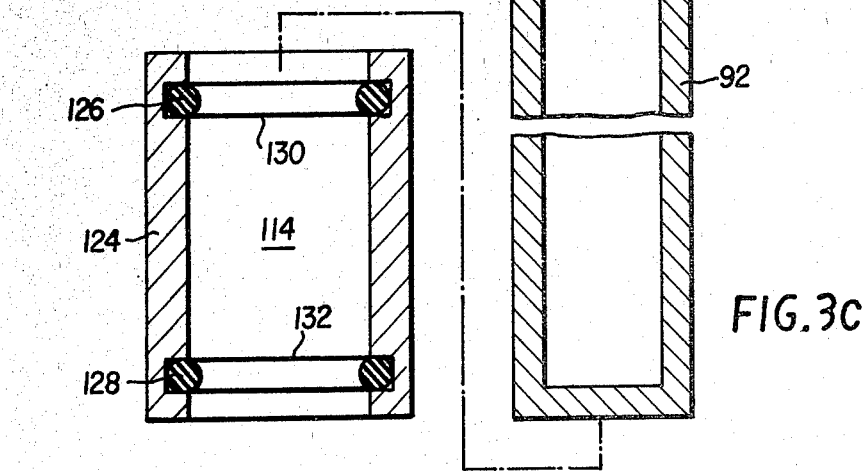
FIG.3b
FIG.3c

DIFFERENTIAL CALORIMETER BASED ON THE HEAT LEAK PRINCIPLE

BACKGROUND OF THE INVENTION

1. Field of the Invention

This invention relates to a differential scanning calorimeter based on the heat leak principle, i.e., to a calorimeter which measures the heat capacity of a sample relative to an appropriate reference as the temperature of the environment surrounding the reference and the sample is scanned through a desired range.

2. Description of the Prior Art

In the past, two basic designs for scanning calorimeters have been used with successful results. These designs represent different philosophies on how to measure heat capacity as a continuous function of temperature. However, both designs depend on the fact that two materials, at the same initial temperature, will have the same final temperature after absorbing identical quantities of heat, if and only if their heat capacities are identical. Thus, when a sample and a reference material, initially at the same temperature, are both heated with the same power to increase the temperature thereof, any difference in heat capacity is expressed as a difference in temperature between the sample and the reference materials. This temperature difference is conveniently measured by a thermocouple, or several thermocouples connected in series (called a thermopile), which generates an easily measured electrical voltage, which in accordance with the Seebeck effect, is directly proportional to the temperature gradient existing across the planar surfaces of the thermopile.

In one basic differential scanning calorimeter (DSC) design, a thermal null is maintained between a reference and a sample as the environmental containing the two is temperature scanned. Generally, DSC's of this type employ electronic circuitry to supply power to a sample heater (or a separate reference heater) as necessary to prevent temperature differences between the reference and the sample. The amount of this power delivered is then directly related to the difference between the heat capacities of the sample and reference materials.

The constraints on this thermal null design are severe, both electronically and thermally. Since it is based upon the principle of maintaining an ideal adiabatic barrier between the calorimeter and the environment, an extensive adiabatic shielding arrangement is required. Furthermore, an extremely sensitive feedback heating system is required to maintain the temperature null between the reference and sample cells.

The other basic DSC design, known as the heat conduction design, dispenses with the active feedback network and simply records thermopiles voltage as a function of temperature as temperature is scanned through a specific range. Such a DSC has been described by Ross et al., Thermochimica Acta, 10 (1974) pages 143–151. While scanning calorimeters of the prior art have demonstrated considerable utility in measuring the energies of transition in solutions, they have for the most part provided only qualitative data with respect to the temperature dependent heat capacities of the samples under test. Furthermore, heat conduction calorimeters found in the prior art have to some extent suffered in sensitivity and accuracy because of thermal gradients existing within the calorimetric equipment.

In addition, the scanning calorimeters found in the prior art are generally designed to operate at only atmospheric pressure, since the introduction of pressure as a calorimetric variable potentially complicates the calorimetric calibration and corrupts the environment of the substances under test. More recently, however, applications have arisen where it is desirable to obtain calorimetric data as a function of pressure. As a result, the need for a sensitive, accurate, and reliable calorimeter which is simple to operate and yet provides calorimetric data at various pressure levels, has arisen.

SUMMARY OF THE INVENTION

Accordingly, one object of this invention is to provide a novel differential scanning calorimeter which is simple to operate and inexpensive to construct.

Another object of this invention is to provide a novel differential scanning calorimeter for measuring the absolute heat capacity of a sample substance.

Yet another object of this invention is to provide a novel differential scanning calorimeter with improved sensitivity and accuracy.

A further object of this invention is to provide a novel differential scanning calorimeter in which sensitivity and accuracy is enhanced as a result of the minimization of thermal gradients existing within the calorimeter.

Yet another object of this invention is to provide a novel differential scanning calorimeter which provides calorimetric data as a function of pressure.

A further object of this invention is to provide a novel differential scanning calorimeter which provides calorimetric data as a function of pressure without requiring recalibration of the calorimeter at the different pressure levels.

Another object of the invention is to provide a novel differential scanning calorimeter wherein positive and negative temperature scanning rates are precisely controlled.

Another object of this invention is to provide a novel method for controlled-temperature scanning a differential scanning calorimeter.

A further object of this invention is to provide a novel method for obtaining calorimetric data as a function of pressure.

A further object of this invention is to provide a novel method for deriving the absolute heat capacity of a substance as a function of temperature.

These and other objects of the present invention are achieved by providing a novel differential scanning calorimeter having a reference measuring cell and a sample measuring cell symmetrically seated within a copper heat sink. Each measuring cell includes a cylindrical stainless steel ampoule which contains a test substance, an aluminum cell frame which supports the ampoule, and a pair of thermopiles which are placed between the aluminum cell frame and the copper heat sink and which measure the temperature difference between the two. The aluminum cell frame is honeycombed to reduce the heat capacity thereof, thereby improving system sensitivity.

The copper heat sink which has end plates connected to conical end sections flanking a middle section is surrounded by a cylindrically copper isothermal shield. A plurality of resistive heating elements are applied to the end plates and conical end sections of the heat sink and the isothermal shield. Each heating element has a resistance proportional to the heat capacity of a respective end plate, conical end middle section or shield, and are judiciously placed on the plural surfaces to constrain thermal gradients within the heat sink in the vicinity of the measuring cells parallel to the longitudinal axis of the heat sink. Thus, by passing a common current through each heating element and by likewise orienting the temperature sensitive surfaces of the thermopiles parallel to the axis of the heat sink, a uniform temperature scan is produced and the effect of residual thermal gradients within the heat sink is minimized.

A cylindrical adiabatic shield surrounds the heat sink and the isothermal shield and minimizes heat loss to the surroundings. The adiabatic shield and the isothermal shield are provided with cooling coils, which are used in conjunction with a microprocessor and the heating elements to generate a highly controlled negative temperature scan.

During operation, calorimetric data are obtained from a baseline scan, a solvent scan and a solute scan. The baseline and solvent effects are then subtracted from the results of the solute scan, and the absolute apparent heat capacity of the solute is derived.

When pressure is a desired calorimetric variable, pressurizable ampoules are employed. The contents of these ampoules are pressurized, the ampoules are sealed and the experiment conducted in the normal manner.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2b is a transverse, sectional view of the aluminum cell taken along the line A—A in FIG. 2a;

FIG. 3a is a sectional side view of a sample or reference ampoule;

FIG. 3b is a sectional side view of one embodiment of a pressurized ampoule;

FIG. 3c is a sectional side view of another embodiment of a pressurized ampoule;

DETAILED DESCRIPTION OF THE PREFERRED EMBODIMENTS

Figure 1A:
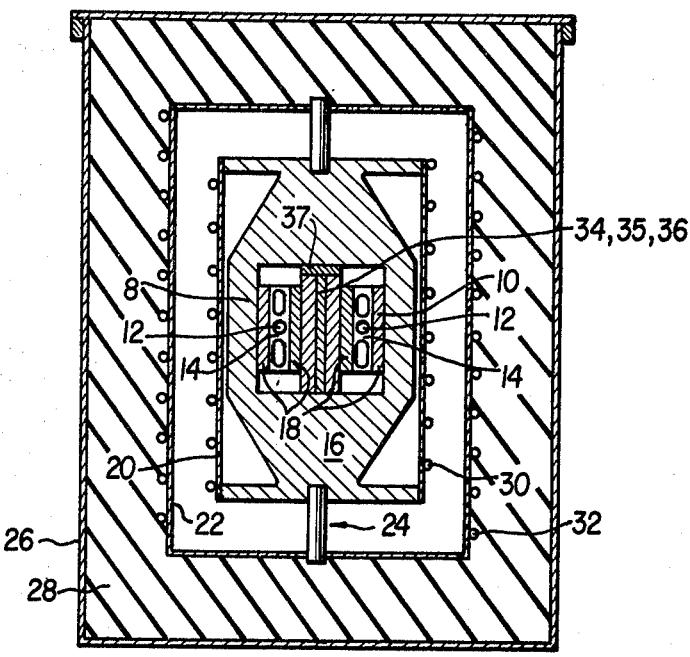
FIGS. 1a and 1b are schematic section top and side views respectively of the calorimeter of this invention.

Referring now to the drawings, wherein like reference numerals designate identical or corresponding parts throughout the several views, and more particularly to FIG. 1 thereof, the calorimeter is seen to consist of a reference measuring cell 8 and a sample measuring cell 10 symmetrically seated within a copper heat sink 16. Each measuring cell 8, 10 includes a cylindrical stainless steel ampoule 12 which contains a test substance, an aluminum cell frame 14 which supports the ampoule 12, and a pair of thermopiles 18 placed between the aluminum cell frame 14 and the copper heat sink 16 and which measure the temperature difference between the two. The measuring cells 8, 10 are maintained in good thermal contact with the copper heat sink 16 by means of three copper wedges 34, 35 and 36 which are angled so as to provide uniform lateral force to each measuring cell 8, 10 thereby maintaining both cells rigidly in place. A fourth smaller wedge 37 perpendicular to the three larger wedges 34–36 and located at the top of these larger wedges, further maintains rigid emplacement of the cell-wedge system in the heat sink 16. A thermal grease, consisting of a silicon base loaded with zinc oxide, is applied to the surface areas of the aluminum cell frames 14, the thermopiles 18, and the wedges 35–37, thereby assuring excellent thermal coupling between the heat sink 16 and each measuring cell 8, 10.

The heat sink 16 is surrounded by a cylindrical copper isothermal shield 20. The combination of the heat sink 16 and the isothermal shield 20 is enclosed within an aluminum adiabatic shield 22 and mechanically coupled thereto by means of plastic support rods 24. The adiabatic shield 22, which houses the heat sink 16 and the isothermal shield 20, is placed inside an outer cylindrical can 26. A polyurthane form 28 is provided between the adiabatic shield 22 and the outer cylindrical can 26 to serve as both an insulative layer, and to hold the adiabatic shield 22 in place within the outer cylindrical can 26.

Figure 1B:
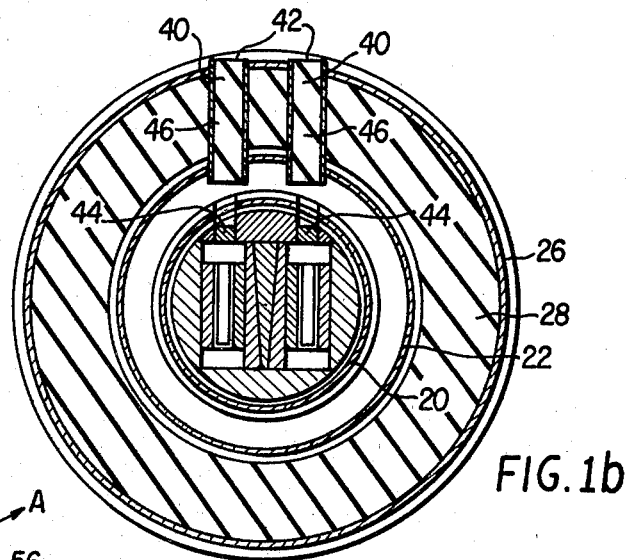

Also shown in FIG. 1a are inner and outer cooling tubes 30 and 32 respectively wound around the isothermal shield 20 and the adiabatic shield 22. As seen in FIG. 1b, each ampoule 12 is loaded into the aluminum cell frame 14 through the outer cylindrical can 26 and the adiabatic shield 22 by means of plastic tubes 40. Also, access openings 42 are provided within the heat sink 16 to enable loading of the ampoules 12 within the aluminum cell frames 14. Once the ampoules 12 are seated within the aluminum cells 14, copper plugs 44 are provided to seal the heat sink access openings 42. Similarly, insulation plugs 46 are inserted within the plastic tubes 40, thereby improving the thermal isolation of the heat sink 16.

Figure 2A:
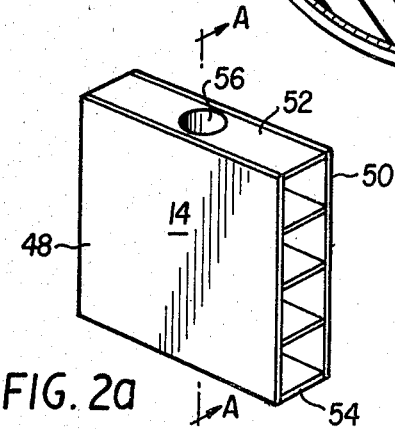
FIG. 2a is a perspective view of an aluminum frame cell which houses a test ampoule.
Figure 2B:
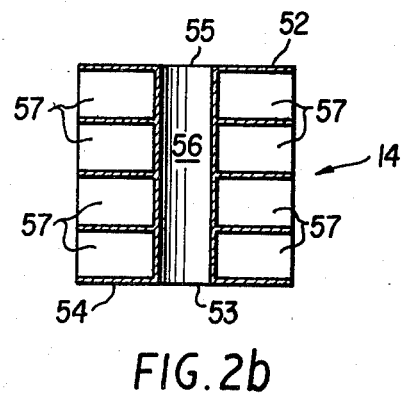

The aluminum cell frame 14 which houses ampoule 12 is seen in FIGS. 2a and 2b to have square aluminum front and rear plates 48 and 50, and rectangular top and bottom plates 52 and 54. Through the center of the frame 14 is drilled a slightly tapered cylindrical boring 56 in which the ampoule 12 is housed. The boring 56 is tapered so that the diameter of the boring exit hole 53 through the rectangular bottom plate 54 is slightly less than the diameter of the boring entry hole 55 through the rectangular top plate 52. The tapered ampoule 12, described hereinafter in detail, has a diameter comparable to the entry hole 55 of the cylindrical boring 56, but slightly larger than the diameter of the exit hole 53, such that the ampoule 12 is rigidly positioned within boring 56 of the frame 14. A plurality of discrete honeycomb cavities 57 are drilled into the cell frame 14 at either side of the cylindrical boring 56. This honeycomb structure reduces the thermal mass (heat capacity) of the cell frame 14 and proportionately improves the instrument sensitivity since the relative contribution of the ampoule to the effective heat capacity is correspondingly increased. In addition, the response time is correspondingly reduced.

The standard calorimeter ampoule 12 seen in FIG. 3a consists of a stainless steel cylinder 58 with a threaded neck orifice 60 through which liquid samples are entered. An air-tight ampoule screw cap 62 with a disposable polyethylene seal 64 is tightened around the ampoule neck orifice 60. The cap 62 and seal 64 provide an air-tight seal, thereby preventing evaporation and anomolous heating effects.

In the event that pressure is selected as a variable, the pressure ampoule shown in FIG. 3b is used. This ampoule has a cylindrical container 66 with a threaded neck orifice 68. A threaded ampoule cap 70 is tightened around the neck orifice 68 whereby the base surface 72 tightly engages an indium seal 74 provided in the shoulder 76 of the neck orifice 68. A stainless steel capillary tube 78 is passed through an opening in the top of the threaded cap 70. The capilliary tube 78 is sliver soldered to the cap 70, thereby maintaining the integrity of the ampoule seal. Within the cap 70 is provided an O-ring 80, a stainless steel evaporation seal 82, and a steel spring 84. The evaporation seal 82 consists of a circular sealing plate 88 with top and bottom guide shafts 86, 87 respectively appending from the top and bottom surfaces of the sealing plate.

During pressurization, the threaded cap 70 is screwed around the neck orifice 68 such that the spring 84 is only loosely tensioned between the sealing plate 88 of the evaporation seal 82 and the top surface 90 of the neck orifice. A pressurized inert gas, such as helium or nitrogen, is forced through the capilliary tube 78, past the evaporation seal 82, and into the cylindrical container 66. Upon attainment of the desired pressure, the threaded cap 70 is tightly screwed around the threaded neck orifice 68 such that the cap base surface 72 contacts the indium seal 74 to seal the pressure ampoule. Concurrently, the steel spring 84 is compressed between the sealing plate 88 and the top surface 90 of the neck orifice 68 such that the sealing plate 88 sealingly engages the O-ring 80 and thereby provides an effective evaporation seal. It is noted that the pressure ampoule shown in FIG. 3b is designed to handle pressures from 1–150 atmospheres and therefore has a wall thickness of 0.065 inches, compared to the 0.015 inch cylinder walls of the standard ampoule shown in FIG. 3a.

Another embodiment of a pressure ampoule, is shown in FIG. 3c. This ampoule also has a cylindrical stainless steel container 92 and a neck orifice 94. A stainless steel threaded cap 96 is designed to engage the neck orifice 94 and thus seal the contents of the ampoule. The threaded cap 96 is provided with an upper threaded opening 98 and a lower threaded opening 100 which engages the threaded neck orifice 94 of the ampoule container 92. The upper and lower threaded openings 98 and 100 are separated by a partition 102. A small access hole 104 is drilled through the partition 102 such that the upper threaded opening 98 communicates with the lower threaded opening 100 by means of the access hole 104. Also, the cap partition 102 is provided with a cylindrical projection 106 from the lower central surface of the partition 102. The projection 106 protrudes into the lower threaded opening 100. An O-ring 108 is fitted around the partition projection 106 in proximity to the access hole 104. A square shoulder 110 is provided to enable wrench tightening of the threaded cap 96 on the neck orifice 94.

Auxiliary pressurization components also shown in FIG. 3c include a pressurization cap 112 and a cylindrical pressurization sealing sleeve 114. Appending from the lower portion of the pressurization cap 112 is a threaded neck orifice 116. A stainless steel capilliary tube 118 is routed through the pressurization cap 112 and through the lower neck orifice 116. An O-ring 120 is seated in a cylindrical recess 122 surrounding the threaded lower neck orifice 116. The pressurization sealing sleeve 114 consists of a stainless steel cylinder 124 provided with upper and lower O-rings 126 and 128 respectively emplaced in upper and lower recesses 130 and 132 machined into the inner wall of the cylinder 114.

When pressurizing the ampoule of FIG. 3c, the lower threaded opening 100 of the threaded cap 96 is loosely screwed onto the neck orifice 94 of the ampoule container 92. The threaded lower neck 116 of the pressurization cap 112 is tightly screwed into the upper threaded opening 98 of the threaded cap 96 such that the upper shoulder 134 of cap 96 enters the cylindrical recess 122 and compresses the O-ring 120 contained therein, thereby effectively sealing the connection of the pressurization cap 112 to the ampoule cap 96. Thereafter, the pressurization sealing sleeve 114 is slid over the ampoule cylindrical container 92 such that the upper O-ring 126 of the sleeve 114 is in contact with the threaded ampoule cap 96, while the lower O-ring 128 is in contact with the ampoule cylinder 92. Since the O-rings 126 and 128 of the pressurization sleeve 114 are tight fitting around the ampoule threaded cap 96 and the ampoule cylindrical container 92, the cylindrical sealing sleeve 114 prevents pressure leakage during pressurization of the ampoule.

Pressurization is accomplished by applying a pressurized inert gas, for example helium or nitrogen, through the stainless steel tube 118, through the threaded cap 96 by means of upper threaded openings 98, access hole 104 and lower threaded opening 100, through the ampoule neck orifice 94, and into the ampoule cylindrical container 92. Upon attainment of the desired pressure level within the ampoule cylinder 92, the threaded lower opening 100 of the ampoule cap 96 is tightened around the threaded neck orifice 94 such that the neck orifice 94 compresses the O-ring 108 against the access hole 104 and the upper surface of threaded opening 100, thus sealing the contents of the ampoule cylinder 92. Thereafter, the pressurization cap 112 is removed from the upper threaded opening 98 of the ampoule cap 96, and the pressurization sealing sleeve 114 is likewise removed from around the ampoule cylinder 92 and the ampoule cap 96. A threaded ampoule handling insert, labeled as 136 in FIG. 3c, is screwed into the upper threaded opening 98 of the ampoule cap 96. The insert 136 is provided with a hook opening 138 which facilitates handling of the ampoule as the ampoule 92 is placed in the cell frame 14 within the heat sink 16.

Figure 4:
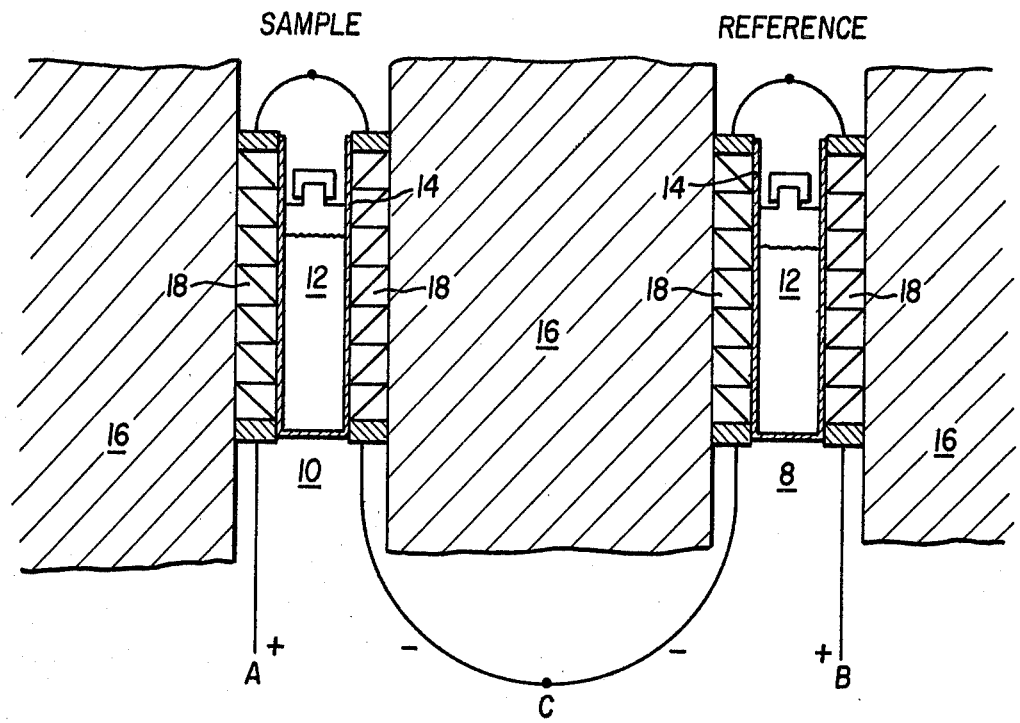
FIG. 4 is a schematic representation of the electrical and thermal connection of the thermopiles within the calorimeter heat sink.

As indicated above, each measuring cell 8, 10 utilizes a pair of thermopiles 18 to measure the temperature differences between the cell frame, which is essentially at the temperature of the test substance, and the heat sink 16. As shown in FIG. 4, the two pair of thermopiles are connected electrically in series with opposite polarity and thermally in parallel. The voltage measured across the thermopiles is therefore $V = V_{AB} = (V_{AC} - V_{BC}) = a(T_s - T_r)$, where V is voltage, $T_s$ and $T_r$ are respectively the temperature of the sample and the reference, and a is the Seebeck coefficient.

Commerically available thermoelectric modules are used for the thermopiles 18. In the past, aluminum base thermoelectric modules have been employed. More recently, ceramic based thermoelectric modules manufactured by the Cambridge Thermionic Corporation (Cambion Model 801-2000-01) have yielded excellent results.

Figure 5:
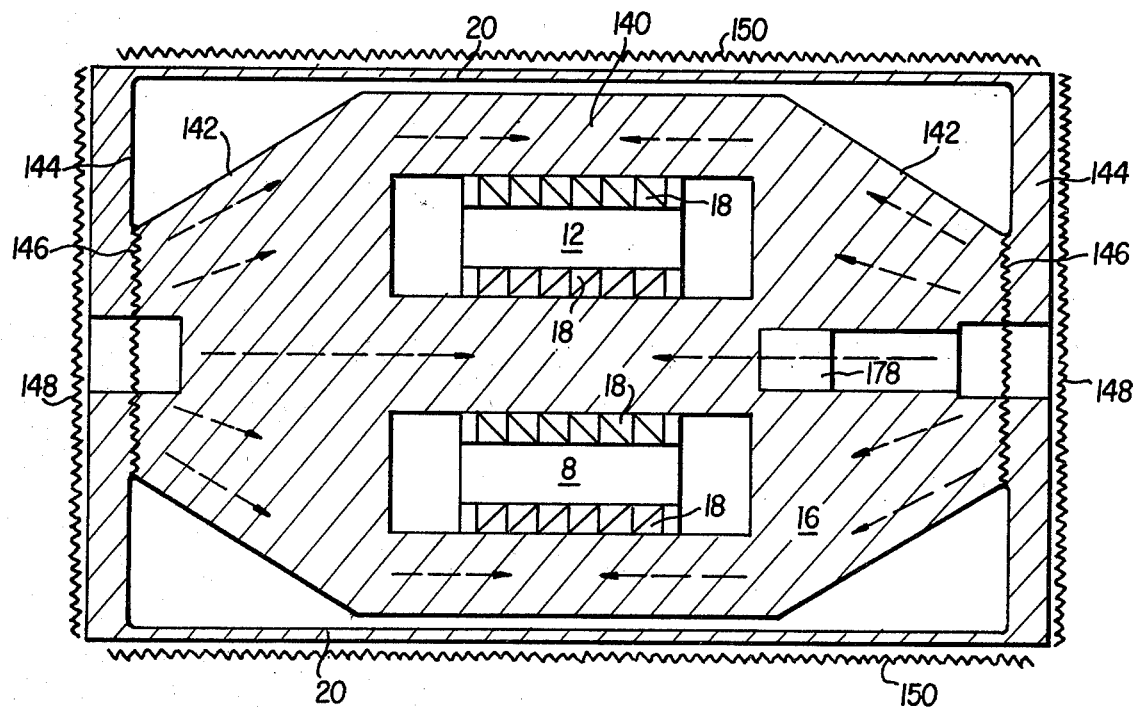
FIG. 5 is a schematic view of the calorimeter heat sink and isothermal shield, showing thermopile orientation and calorimeter heater placement.

The calorimeter heat sink 16, as shown schematically in FIGS. 1 and 5, is machined from copper for good thermal conductance and high thermal mass (approximately 80 times the thermal mass of each measuring cell 8, 10). Since operation of the calorimeter is based on the assumption of uniform temperature within the heat sink 16, i.e. no thermal gradients within the heat sink 16, the shape of the heat sink 16 is designed to minimize the existence of these thermal gradients. The heat sink 16 is therefore provided with a cylindrical middle section 140 which converges into conical end sections 142 on either side of the cylindrical middle section and terminates with circular plates 144 which have a diameter slightly greater than the diameter of the central cylindrical section 140. The cylindrical middle section 140, conical end sections 142 and circular plates 144 are all machined from a single piece of copper. Surrounding the heat sink cylindrical center section 140, conical end sections 142, and end plates 144 is the copper isothermal shield 20 which is attached to the end plates 144.

A plurality of heating elements are placed around the heat sink 16 in order to scan the temperature of the heat sink. As schematically shown in FIG. 5, the two heaters labeled 146 and located at the intersection between the conical end sections 142 and the heat sink end plates 144 provide heat to the heat sink conical end sections 142 and the cylindrical center section 140 between them. The heaters labeled 148 are applied to the surfaces of the heat sink end plates 144 and provide heat to these plates. The heater labeled 150 is attached to the isothermal shield 20 to provide heat to the cylindrical shield 20. Each of the heater elements 146, 148 and 150 consist of resistive heaters wired in series and connected to a common power supply.

In deriving the resistance values for the heating elements 146, 148 and 150, it is noted that the heat sink scanning rate $\alpha$ is defined as $$\alpha = dT/dt = dT/dQ \cdot dQ/dt \qquad (1)$$

wherein T is temperature, t is time, and Q is energy (heat). Since the sink heat capacity is $C_p = dQ/dT$, $$\alpha = 1/C_p \cdot dQ/dt = 1/C_p \cdot W = 1/C_p \cdot V_{DC} \cdot I \qquad (2)$$

wherein $V_{DC}$ is the power supply voltage (D.C.) across the electrical heater elements 146, 148 and 150; I is the current through the heater elements; and W is the watts of power supplied. Since each of the resistive heating elements 146, 148 and 150 are wired in series, they each have the same electrical current passing through them. From Ohm's law $V = IR$, wherein R is the total heater resistance, and therefore, $$\alpha_i = C_{p_i}^{-1} \cdot I^2 \cdot R_i \qquad (3)$$

By selecting the resistance of each heater element $R_i$ as proportional to the heat capacity, $C_{p_i}$, of the isothermal shield and that part of the heat sink to which the heater elements Ri respectively provide heat as above indicated then each part of the heat sink and the isothermal shield experiences the same scanning rate; i.e., all $\alpha_i$ are equal, and thus internal thermal gradients within the heat sink 16 are considerably reduced.

As seen in FIG. 5, thermal gradients within the heat sink during temperature scanning are geometrically constrained along the axis of the heat sink, parallel to the direction of the arrows, as a result of the uniform heating produced by the heating elements 146, 148 and 150. Since the thermopiles 18 are sensitive to temperature differentials existing across their planar surfaces, the thermopiles 18 of each measuring cell 8, 10 are oriented parallel to the temperature gradients within the heat sink 16, and are therefore unaffected thereby. Thus the thermopiles 18 only measure temperature differences between the heat sink and the aluminum cell frame 14, and a major source of calorimetric error is eliminated.

In one embodiment (shown in FIG. 5), the heating elements 146, 148 and 150 are fabricated from non-inductively wound manganin wire. In another embodiment, the manganin heater wire elements are replaced with etched foil heater elements that paste onto the metal surfaces of the heat sink 16 and the isothermal shield 20. In the second embodiment the separate heater element 146 is eliminated. These foil heater elements designed by the petitioners and made by MINCO, INC., Minneapolis, Minnesota, maintain the prescribed heater density distribution on the various surfaces, and greatly simplify assembly and repair of the calorimeter heater.

It has been found that supplying 13 watts of power from a regulated D.C. power supply having constant voltage output results in a heat sink temperature scanning rate of $15 \pm 3\%$ °C./hr between 5° C. and 75° C. The several percent deviation in scanning rate constancy is believed to be due to the temperature dependence of the resistance of the heating elements 146, 148, and 150, along with the temperature dependence of the heat capacity of copper. Furthermore, this scanning rate is constant within these limits only in the absence of heat gain or loss by the heat sink 16 to the surroundings. To reduce or eliminate these effects, the adiabatic shield 22 is incorporated into the calorimeter and surrounds the heat sink 16 and isothermal shield 20.

The adiabatic shield 22 consists of an aluminum closed cylinder having a resistive heater element 152 applied to its exterior cylindrical surface. The heater element 152 is made of either hand wound manganin wire (first embodiment) or paste on foil heater elements (second embodiment). The adiabatic shield heater element 152 is powered by a power amplifier 154 under the control of a precision temperature controller 156 shown in FIG. 6. The precision temperature controller 156 senses the reference temperature of the heat sink surface from the resistance of a nickel wire wound uniformly on the outside surfaces of the copper isothermal shield 20, and the temperature of the aluminum adiabatic shield from a nickel wire uniformly wound on its exterior surface. These nickel temperature sensing wires are respectively labeled as 158 and 160 in FIG. 6. A resistance bridge within the precision temperature controller 156 compares the resistance of the nickel temperature sensing wires 158 and 160, and hence the temperature of the heat sink 16 and the adiabatic shield 22. The power amplifier 154 is then directed by the precision temperature controller 156 to supply the heater element 152 with sufficient power to maintain the temperature of the adiabatic shield 22 the same as that of the heat sink 16, thereby eliminating heat gain or loss from heat sink 16 to the environment.

The temperature control required on the adiabatic shield 22 is not critical; temperature differences on the order of 1° C. or less are adequate. In that respect, deviations from the ideal constant scanning rate are accounted for by calculating the exact instantaneous scanning rate and compensating for scanning rate deviations in the data analysis described hereinafter.

It is noted that the heater elements 146, 148, 150 and 152 in addition to the nickel temperature sensing wires 158 and 160 are applied non-inductively to the various metal surfaces of the heat sink 16, the isothermal shield 20 and the adiabatic shield 22.

Figure 6:
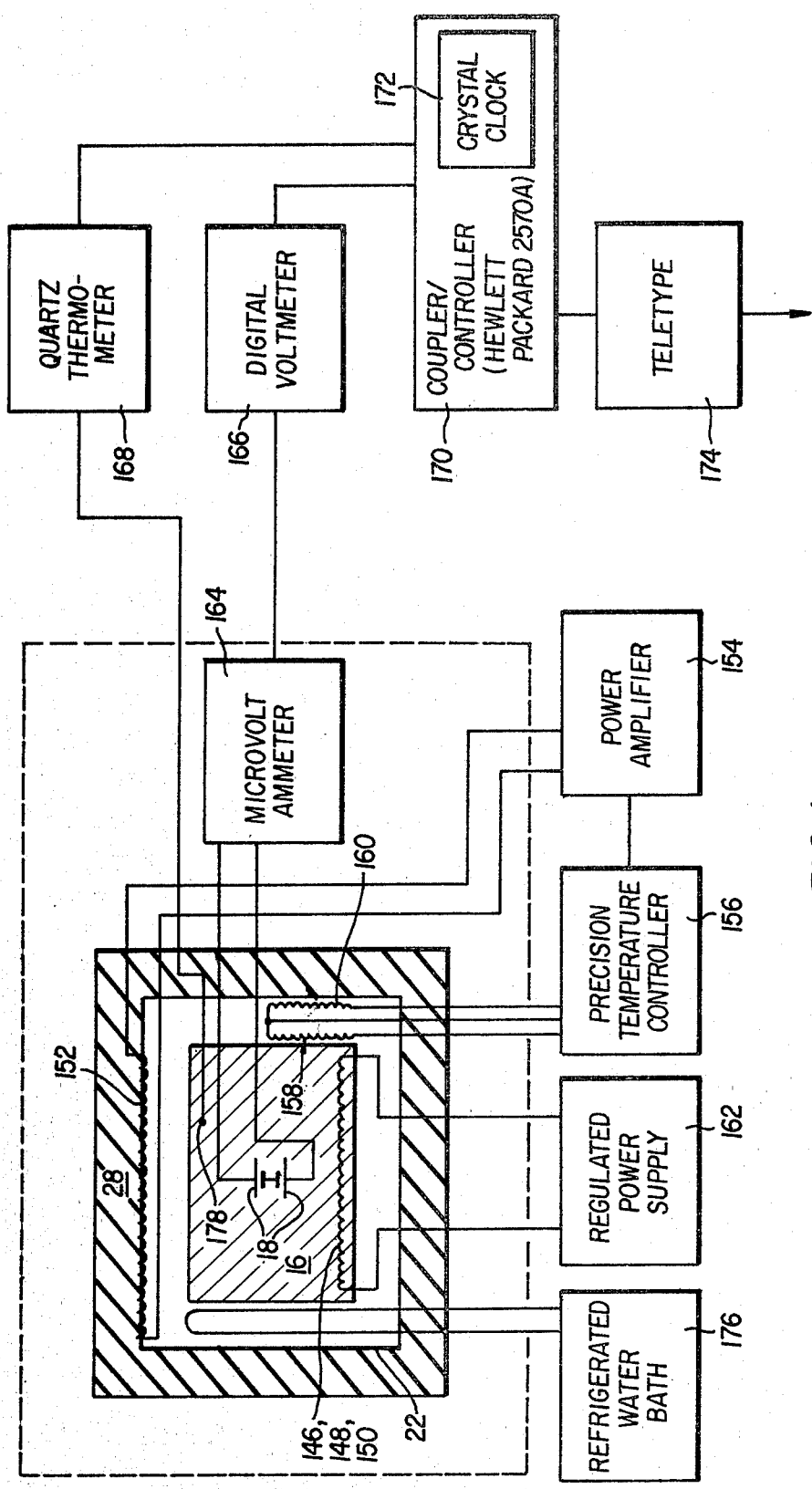
FIG. 6 is a system diagram of the calorimeter of the invention, including auxiliary components for temperature control and data collection.

A system diagram of the calorimeter, including auxiliary components for temperature control and data collection, is shown in FIG. 6. These auxiliary components include: the regulated constant voltage power supply 162; the precision temperature controller 156; the power amplifier 154; a microvolt ammeter 164; a digital voltmeter 166; a quartz thermometer 168; a coupler controller 170 having a crystal clock 172; a teletype 174; and a refrigerated water bath 176.

Operation of the regulated constant voltage power supply 162, the precision temperature controller 156, and the power amplifier 154 is as discussed above.

The differential thermopile voltage is amplified by the microvolt amplifier 164 and digitized by the digital voltmeter 166, before being applied to the coupler/controller 170. The heat sink temperature is measured by the quartz thermometer 168 provided with a temperature sensitive quartz crystal probe 178. The probe 178 is located on the axis of the copper heat sink near the cell compartment, as shown in FIG. 5. This quartz thermometer 168 consists of a counter which measures the temperature dependent frequency of a quartz crystal oscillator and is calibrated so that the integrated frequency read out of the counter is directly in degrees centigrade. The coupler/controller 170 (Hewlett-Packard Model 2570A) executes a program which generates a reading of heat sink temperature (T) from the quartz thermometer 168, the amplified thermopile voltage (V) from the digital voltmeter and the clock time (t) at which those readings were initiated. The output of the coupler controller 170 is interfaced to a teletypewriter which then records the data (T, V, t) onto paper tape. Upon completion of a calorimetric experiment, the data recorded on paper tape is then read into a storage file of a time shared computer for analysis. A computer program, called "SCAN" then processes the experiment data in one of three selected modes of operation, as discussed hereinafter.

Before discussing calorimetric data analysis, the relationship between various measured parameters is now described.

The assumption of thermal equilibrium within the cells (experimentally verified), along with the definition of the Seebeck effect (the thermopile voltage is directly proportional to the temperature difference), Newton's cooling law, and the conservation of energy yield the following equation (4) describing the thermal properties of one cell (sample or reference) while temperature is raised at a constant rate:

$$C_P = \epsilon/\alpha(V + \tau \cdot dV/dt - A \cdot V) \quad (4)$$

wherein $C_P$ is the total cell heat capacity, $\epsilon$ is a calibration constant (equal to the ratio of the thermopile thermal conductance to the Seeback coefficient), $\alpha$ is the temperature scanning rate (dT/dt), V is the thermopile voltage, (dV/dt) is its time derivative, $\tau$ is the cell thermal response time (equal to the ratio of the cell heat capacity to the thermopile thermal conductance), and A is a small higher order correction term due to the temperature dependence of the Seebeck coefficient. The calibration parameters $\epsilon$, $\tau$, and A, which are functions of temperature, are determined by electrical calibration of each measuring cell at different temperatures by putting known electrical power into a small heater contained within the measuring cell, and measuring the calorimetric response. The thermopile voltage V, and heat sink temperature T are recorded as a function of time during a given scanning experiment, and thus the voltage time derivative dV/dt, and scanning rate dT/dt can be readily computed.

When a scanning experiment is performed with both sample and reference cells empty, there is a finite, non-constant differential thermopile voltage generated as a function of temperature. For the calorimeter of the invention scanning at 15° C./hr; this voltage is ~100 μv lower at 75° C. than it is at 5° C., and is a smooth monotonic function of temperature. These finite voltages are due to two effects. Firstly, any residual heat sink gradients perpendicular to the thermopile planar faces voltage if they are not exactly symmetrical about the measuring cells 8, 10 will produce an apparent temperature difference. This effect has been minimized by the design of the heat sink and placement of heaters as discussed above. Secondly, the thermal properties of the thermopiles cannot be exactly matched at all temperatures, and therefore their voltage response will not exactly cancel at all times, yielding a finite measured net voltage which varies with temperature. This non-zero changing voltage response with temperature can therefore be considered as an instrumental baseline, and variations from this baseline measured with the ampoules containing a reference and sample material are then considered as voltage signals proportional to heat capacity differences. The instrumental baseline of the described calorimeter is reproducible from one scanning experiment to the next on the order of ±100 μcal/deg in heat capacity over the range 5° C. to 75° C., at a scanning rate of 15° C./hr. Therefore, absolute heat capacities can be calculated to that order of precision.

The reproducibility of the baseline is due to the careful design of the heat sink 16, the isothermal shield 20 and the heaters 146, 148 and 150 which produce the high degree of thermal symmetry between reference and sample cells. The absolute voltage level for a baseline scan at any temperature depends on the relative masses of material loaded into the reference and sample cells, whereas the shape of the monotonically changing voltage-temperature baseline is reproducible for a given scanning rate, for any combination of material masses selected.

In practice the absolute heat capacity is calculated by first doing an experimental scan with a known amount of pure water in both the reference and sample ampoules. The instrumental baseline response is then obtained and recorded on paper tape. Water is chosen as the baseline material because the heat capacity of water is well known as a function of temperature. Therefore, by comparing the stored water baseline with the instrumental response generated by an unknown sample relative to a water reference, the relative heat capacity of the sample can be determined. Since the absolute heat capacity of water is well documented, the absolute heat capacity of the sample can be readily calculated.

In describing the experimental procedure of the invention, it is noted that this procedure is the same for a water baseline scan or a sample scan. The stainless steel ampoules 12 are removed from the calorimeter, washed and dried and loaded using a syringe and hypodermic needle. The total mass of sample or water is determined by weighing (to ±0.00001 g) the ampoule before and after filling with 0.6 to 1 cc of material. The ampoules 12 are pressurized if desired, and tightly sealed to prevent evaporation and hence large anomalous heating effects. The ampoules are placed into the calorimetric cells through the fill holes provided, the copper plugs 44 are positioned into the heat sink openings, and the insulation plugs 46 are inserted. The calorimeter is usually loaded in this way at room temperature or above to prevent possible water vapor condensation inside the opened calorimeter at low temperatures. If data is required below room temperature, the refrigerated water bath 176 is turned on to circulate cold water through the cooling coils 30, 32 in order to cool the calorimeter down to the desired starting temperature. During this cool down period, dry nitrogen gas is usually bled into the air space between the heat sink 16 and the adiabatic shield 22 to maintain a dry atmosphere within the heat sink 16 and to thereby prevent water condensation and subsequent evaporation during a scan.

Thermal equilibrium of the heat sink contents at or near the thermostat controlled bath setting is determined by a negligible voltage reading from the thermopiles. At this time the scanning experiment is initiated by shutting off the cooling water bath 176 and turning on the voltage regulated power supply 162 at a voltage level required to give the desired scanning rate; e.g., 13 watts provides a scan rate of 15° C./hr. There is an approximate 15-20 minute start-up period before the voltage signal reaches its steady-state value. Typically, the start-up exhibits a rapid departure from zero voltage and asymptotically approaches the steady state value (determined by the masses of material in each cell and the scanning rate) after 15-20 minutes. Only after attainment of steady state conditions do the assumptions used in deriving the relevant equations hold. This lag time before collection of data can begin means that it is necessary to initially cool the calorimeter below the desired minimum temperature for heat capacity data; approximately 4° to 5° C. when $\alpha = 15°$ C./hr. During this time the dry nitrogen gas flow is shut off, and the precision temperature controller 156 driving the adiabatic shield 22 has more than ample time to adjust the shield temperature to that of the heat sink. The sink heater power supply and shield controller then remain without any further adjustment for the duration of the scanning experiment.

When the desired high temperature of the scan is reached in the heat sink 16, the experiment is terminated by shutting off the sink heater power supply 162, the precision temperature controller 156, and the data collection devices. The calorimeter can then be cooled down by activating the refrigerated water bath 176.

During data analysis, the experimental data (T, V, t) is read into a file on a time shared computer for analysis. The data is then processed in one of three selected modes of operation of the program "SCAN". The water baseline data, i.e. the values of T, $\alpha$, V, dV/dt, $V_2$, and $dV_2/dt$ where T is the heat sink temperature, $\alpha$ is its time derivative, dT/dt, V and dV/dt refer to the differential thermopile voltage, and $V_2$ and $dV_2/dt$ refer to the calculated values of the reference cell thermopiles, at every calculated 0.1 deg interval of the sample cell temperature, are stored in a baseline file. For a scanning rate $\alpha$ of 15° C./hr, $V_2 \approx 12$ mV while $V = V_{AC} - V_{BC} \pm 50$ $\mu$V. The stored values are calculated from a least squares fit of the values of T, V, and $V_2$ as second order polynomial functions with time over an approximate 2 degree range of temperature centered around the calculated time at which the cell temperature was the desired value.

The second operational mode is for analysis of data obtained from a scanning experiment in which the experimental solvent (buffer) is loaded in the sample ampoule. The solvent heat capacity is calculated and stored in another computer file for every 0.1° C. in order to subtract that portion of the experimental heat capacity due to the solvent from the solution of interest.

The third operational mode is for analysis of the heat capacity of a solute in the experimentally scanned solution. In this mode, the values T, V, $V_2$ and each respective time derivative are also calculated from sliding second order polynomials centered around each 0.1° C. cell temperature over an appropriate temperature range. The experimental heat capacity is then calculated by comparing these solution variables with those of the preceding water baseline values stored in the computer file. The instrumental parameters such as $\epsilon$ and $\tau$ for each cell are calculated at the appropriate temperature using stored coefficients of second order polynomial fits of each parameter with temperature, as determined from a previous series of electrical calibrations at different temperatures. After subtracting the value of the solvent heat capacity contribution, the remaining calculated heat capacity in calories/degree is divided by the known mass of solute and printed out as solute heat capacity in calories per gram-degree at every 0.1° C. interval of sample cell temperature. The essence of the computer operation is the subtraction of the instrumental baseline, and then the transformation of the voltage as a function of time into heat capacity as a function of temperature.

Figure 7:
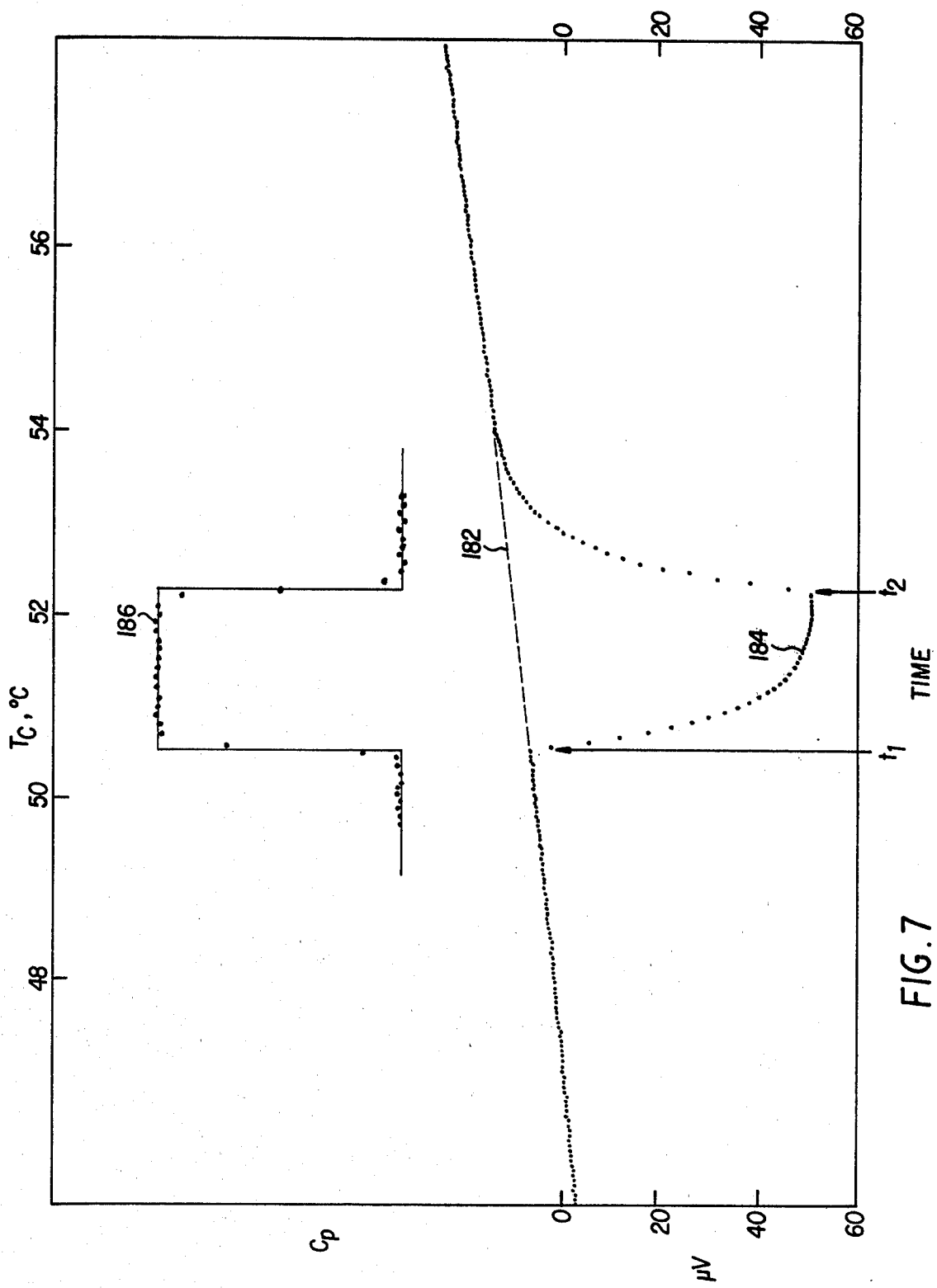
FIG. 7 is a graph of baseline data and the voltage signal obtained when a square pulse of power is applied to the calibration heater in the reference cell of the calorimeter of the invention; also shown is the signal corrected for the time response of the calorimeter and converted to an apparent heat capacity.

An example of the data analysis is shown in FIG. 7, where a single data transformation is shown. The curve labeled 184 corresponds to differential thermopile voltage data collected every 13 sec for a water baseline scan with the power supply 162 delivering 13 watts of power to the heater elements 146, 148 and 150, resulting in a calorimetric scanning rate ($\alpha$) of 15° C./hr. The curve labeled 184 is a simulation of the heat capacity of an unknown sample obtained by repeating the scan of curve 182 while adding heat to the sample cell through the 50 $\Omega$ sample cell calibration heater. This heat is generated from an external regulated constant current (D.C.) source with a precise timing control, and for curve 184 was turned on ($t_1$ on FIG. 7) at 4 mA; seven minutes later ($t_2$ on FIG. 7) the heater was automatically shut off. Therefore, the difference between curves 184 and 182 is the differential thermopile voltage generated by a constant heat effect of +0.2 mcal/sec inside the sample cell for the seven minutes between times $t_1$ and $t_2$ (total heat input=85 mcal) and a zero heat effect elsewhere. Curve 184 was computer analyzed as described using program "Scan" in the solvent mode, with the previously calculated data from curve 182 stored in the baseline file. The results of this calculation are shown for every 0.1° C. of the sample cell as an apparent heat capacity in curve 186 in FIG. 7. The calculated total heat effect, from integration of curve 186, is 85 mcal ±0.1%. The solid curve through the calculated values of 186 is the shape of the known electrical heat effect. The same values of 186 can be obtained from the program "Scan" in the solute mode by proper manipulation. At least two effects of the computer calculation are seen in FIG. 7; the nonconstant baseline voltage effect is removed since the difference between 182 and 184 is zero outside the $t_1 \rightarrow t_2$ range; the slowly changing voltage following $t_1$ and $t_2$ on 184 is due to the time response of the sample cell, and is corrected for in the computer program, yielding the correct square wave shape of 186. These are the two major effects of the computer program "Scan" during the transformation of the calorimetric raw data (T, V, t) into the desired heat capacity as a function of temperature.

In another embodiment, the differential scanning calorimeter of the invention is interfaced with a PDP 11/10 minicomputer whereby the entire experimental procedure is automated. As a result, approximately forty times as much voltage data is collected at a considerably faster rate. Calorimeter precision is thereby improved through the concomittant noise reduction (from ±25 μcal/degree to approximately ±4 μcal/degree), and furthermore the shape of the heat capacity curve is more precisely defined.

The addition of a microprocessor to control the calorimetric experiment also results in a major improvement in the reproducibility of the scanning rate from the original ±3–4% to ±0.03%. This is accomplished by replacing the constant voltage regulated power supply 162 which heats the heaters 146, 148 and 150 with a programmable power supply under the control of the microprocessor. A conventional programmable power supply may be used, e.g. such as a KEPCO, Inc., Flushing, N.Y. model number JQE 0–100 v, 0-1A unit. The minicomputer then accepts digital temperature data from thermometer 168, calculates in real time the instantaneous temperature scanning rate $\alpha$, and generates a precise temperature scanning control signal. This signal is then applied by means of a digital-to-analog converter to the programmable power supply which in turn powers the heat sink heater elements 146, 148 and 150.

As a result of the improved reproducibility of the scanning rate $\alpha$, this calorimetric parameter can be assumed to be identically constant for each of the baseline, solvent and solute temperature scans. Accordingly, during data analysis it is no longer necessary to compensate for variations in $\alpha$, and the analysis is thereby significantly simplified.

Yet another substantial benefit derived by the introduction of the microprocessor into the calorimeter system is the fact that highly accurate negative temperature scans, i.e. from high temperature to low temperature, may be possible. This is accomplished by using the refrigerated water bath 176 in conjunction with the cooling coils 30, 32 to establish control of the negative temperature scan. The digital-to-analog feedback control system discussed above is then employed to tightly control the constancy and accuracy of the rate of temperature decrease of the calorimeter.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A differential scanning calorimeter based on the heat leak principle comprising:

a thermally conductive heat sink having a cylindrical middle section, conical end sections adjacent to both ends of said middle section, and end plates integrally attached to said conical end sections, said heat sink having a longitudinal axis through the center of said middle section, said conical end sections and said end plates;

a pair of heat capacity measuring cells symmetrically disposed within said middle section of said heat sink, one of said measuring cells containing a reference substance, and the other of said cells containing a sample substance;

a cylindrical isothermal shield attached to said end plates and surrounding said heat sink;

temperature scanning means attached to the end plates and the conical end sections of said heat sink and to said isothermal shield for adding an amount of heat to said end plates, conical and middle sections, and shield in proportion to the heat capacity of said end plates, said conical and middle sections and said shield;

temperature monitoring means for measuring the temperature of said heat sink at various points in time during a temperature scan; and adiabatic shield means surrounding said isothermal shield for preventing heat loss or gain from said heat sink and said isothermal shield;

whereby said temperature scanning means uniformly heats said heat sink such that any thermal gradients within said middle section of said heat sink are essentially constrained parallel to said longitudinal axis of said heat sink.

2. A differential scanning calorimeter according to claim 1, wherein each of said heat capacity measuring cells comprises:

ampoule means for containing said test or said reference substances;

cell frame means, housing said ampoule means, for supporting said ampoule means, said cell frame means thermally conductive and at least partially honeycombed such that the heat capacity of said cell frame means is reduced; and temperature differential sensing means in contact with said heat sink and said cell frame means for measuring the temperature differential between said heat sink and said cell frame means.

3. A differential scanning calorimeter according to claim 2, wherein said temperature differential sensing means comprises:

a pair of thermopiles, each of said thermopiles having a pair of planar surfaces, said thermopiles measuring the temperature gradient existing perpendicular to said planar surfaces, said thermopiles oriented with said planar surfaces parallel to said longitudinal axis of said middle section of said heat sink;

whereby said thermopiles are unaffected by temperature scanning thermal gradients produced in said heat sink parallel to said longitudinal axis of said heat sink.

4. A differential scanning calorimeter according to claim 2, wherein said ampoule means comprises:

a pressurizable ampoule.

5. A differential scanning calorimeter according to claim 4, wherein said pressurizable ampoule comprises:

a cylindrical ampoule container having a threaded neck orifice at one end of said container, said neck orifice having a flat top surface, and a flat shoulder surface at the base of said neck orifice;

disposable sealing means seated within said shoulder of said neck for providing said ampoule means with an air-tight seal;

a threaded cap which matingly engages said threaded neck orifice, said cap having a flat bottom surface which sealingly engages said disposable sealing means when said cap is screw tightened on said threaded neck orifice;

capillary tubing means embedded in said threaded cap for applying a pressurized inert gas to said ampoule means; and evaporation sealing means within said threaded cap for producing an air-tight evaporation seal within said ampoule means after pressurization of said ampoule through said capillary tubing means.

6. A differential scanning calorimeter according to claim 5, wherein said evaporation sealing means of said ampoule means comprises:

an elastomeric O-ring seated against the top interior surface of said threaded cap, said O-ring having a central opening in communication with said capilliary tubing means;

an evaporation seal having a circular sealing plate with top and bottom guide shafts respectively appending from the top and bottom surfaces of said sealing plate, said top guide shaft maintaining said sealing plate directly beneath said O-ring; and, spring tensioning means seated on said top flat surface of said threaded neck orifice between said sealing plate and said top flat surface;

whereby after pressurization of said ampoule means and tightening of said threaded cap on said threaded neck orifice, said spring tensioning means applies a force to said sealing plate, forcing said plate against said O-ring and providing an air-tight seal between said ampoule container and said capilliary tubing means.

7. A differential scanning calorimeter according to claim 4, wherein said ampoule means comprises:

a cylindrical ampoule container having a first threaded neck orifice at one end of said container, said neck orifice having a flat top surface;

an ampoule cap comprising threaded upper and lower openings, said lower threaded opening threadingly connected to said first threaded neck orifice, a partition separating said upper and lower openings, said partition having a cylindrical recess drilled in the bottom surface of said partition, said recess in communication with said lower threaded openings; an access hole drilled through said partition connecting said upper threaded opening to said cylindrical recess and said lower threaded opening; and first sealing means seated in said cylindrical recess;

removeable pressurization means, threadingly connected to said ampoule cap, for pressurizing said ampoule means; and removeable pressurization sealing means, surrounding the threaded connection between said lower threaded opening of said ampoule cap and said ampoule container, for sealing said threaded connection during the pressurization of said ampoule means;

whereby said ampoule means is pressurized by said pressurization means whereupon said lower threaded opening of said ampoule cap is threadingly tightened on said first threaded neck orifice of said ampoule container, said top surface of said threaded neck orifice compressing said first sealing means seated in said cylindrical recess against said access opening, thereby sealing said pressurized ampoule means, said pressurization means and said pressurization sealing means thereafter disconnected from said ampoule cap and said ampoule container.

8. A differential scanning calorimeter according to claim 7, wherein said removeable pressurization means comprises:

a pressurization cap having a second threaded neck orifice which matingly engages said upper threaded opening of said ampoule cap, said pressurization cap further having a second cylindrical recess surrounding said second threaded neck orifice;

second sealing means, disposed in said second cylindrical recess, for providing an air-tight seal between said pressurization cap and said ampoule cap when said second threaded neck orifice is tightly connected to said upper threaded opening of said ampoule cap; and, capilliary tubing means embedded in said pressurization cap for applying a pressurized inert gas to said ampoule container through said pressurization cap and said ampoule cap.

9. A differential scanning calorimeter according to claim 1, wherein said temperature scanning means comprises:

a pair of first resistance heating elements, each having a resistance proportional to the heat capacity of the end plates, applied to the surface of said end plates for providing heat to said end plates;

a pair of second resistance heating elements, each having a resistance proportional to the heat capacity of said conical end sections and said middle section, applied to the heat sink in the vicinity of the intersections between the end plates and the conical end sections for providing heat to said conical end sections and said middle section;

a third resistance heating element having a resistance proportional to the heat capacity of the isothermal shield attached to said isothermal shield for providing heat thereto;

said resistive heating elements connected electrically in series; and power supply means connected to said series connected resistive heating elements for applying a common current to each of said heating elements.

10. A differential scanning calorimeter according to claim 9, wherein each of said resistive heating elements comprise:

non-inductively wound manganin wire.

11. A differential scanning calorimeter according to claim 9, wherein each of said resistive heating element comprise:

an etched foil heater element.

12. A differential scanning calorimeter according to claim 9, wherein said temperature scanning means further comprises:

processor control means coupled to said temperature monitoring means for computing an instantaneous temperature scanning rate at said various points in time, and for generating a feedback control signal proportional to the difference between said computed instantaneous temperature scanning rate and a predetermined temperature scanning rate;

programmable power supply means coupled to said calculating means and said plurality of heating elements for applying power to said heating elements in accordance with said feedback control signal generated by said processor control means.

13. A differential scanning calorimeter according to claim 12 wherein said temperature scanning means further comprises:

a source of cold fluid;

cooling coils connected to said source of cold fluid, said cooling coils surrounding said isothermal shield and said adiabatic shield and reducing the temperature of said heat sink upon application of cold fluid through said cooling coils;

whereby a negative temperature scan of said heat sink from high to low temperatures is produced by said cold fluid in said cooling coils, said processor control means, said programmable power supply means and said heating elements providing fine control of said negative temperature scan.

14. In a differential scanning calorimeter for measuring the absolute heat capacity of a sample substance, said calorimeter having a pair of measuring cells containing a reference and a sample substance, said cells disposed in a thermally conductive heat sink, the improvement of each of said measuring cells comprising:

ampoule means for containing a test substance;

cell frame means, housing said ampoule means, for supporting said ampoule means, said cell frame means thermally conductive and at least partially honeycombed such that the heat capacity of said cell frame means is reduced; and temperature differential sensing means in contact with said heat sink and said cell frame means for measuring the temperature differential between said heat sink and said cell frame means.

15. In a calorimeter according to claim 14, the improvement of said ampoule means further comprising:

pressurizable ampoule means.

16. In a calorimeter according to claim 15 the improvement of said pressurizable ampoule means comprising:

a cylindrical ampoule container having a threaded neck orifice at one end of said container, said neck orifice having a flat top surface, and a flat shoulder surface at the base of said neck orifice;

disposable sealing means seated within said shoulder of said neck for providing said ampoule means with an air-tight seal;

a threaded cap which matingly engages said threaded neck orifice, said cap having a flat bottom surface which sealingly engages said disposable sealing means when said cap is screw tightened on said threaded neck orifice;

capilliary tubing means embedded in said threaded cap for applying a pressurized inert gas to said ampoule means; and evaporation sealing means within said threaded cap for producing an air-tight evaporation seal within said ampoule means after pressurization of said ampoule through said capillary tubing means.

17. In a calorimeter according to claim 16 the improvement of said evaporation sealing means comprising:

an elastomeric O-ring seated against the top interior surface of said threaded cap, said O-ring having a central opening in communication with said capilliary tubing means;

an evaporation seal comprising a circular sealing plate having top and bottom surfaces; top and bottom guide shafts respectively appending from said top and bottom surfaces of said sealing plate, said guide shafts maintaining said sealing plate directly beneath said O-ring; and spring tensioning means seated on said top flat surface of said threaded neck orifice between said sealing plate and said top flat surface;

whereby after pressurization of said ampoule means and tightening of said threaded cap on said threaded neck orifice, said spring tensioning means applies a force to said sealing plate, forcing said plate against said O-ring and providing an air-tight seal between said ampoule container and said capilliary tubing means.

18. In a calorimeter according to claim 15 the improvement of said pressurizable ampoule means comprising:

a cylindrical ampoule container having a first threaded neck orifice at one end of said container, said neck orifice having a flat top surface;

an ampoule cap comprising threaded upper and lower openings, said lower threaded opening threadingly connected to said first threaded neck orifice; a partition separating said upper and lower openings, said partition having a cylindrical recess drilled in the bottom surface of said partition, said recess in communication with said lower threaded openings; an access hole drilled through said partition connecting said upper threaded opening to said cylindrical recess and said lower threaded opening; and first sealing means seated in said cylindrical recess;

removeable pressurization means, threadingly connected to said ampoule cap, for pressurizing said ampoule means; and removeable pressurization sealing means, surrounding the threaded connection between said lower threaded opening of said ampoule cap and said ampoule container, for sealing said threaded connection during the pressurization of said ampoule means;

wherein said ampoule means is pressurized by said pressurization means whereupon said lower threaded opening of said ampoule cap is threadingly tightened on said first threaded neck orifice of said ampoule container, said top surface of said threaded neck orifice compressing said sealing means seated in said cylindrical recess against said access opening, thereby sealing said pressurized ampoule means, said pressurization means and said pressurization sealing means thereafter disconnected from said ampoule cap and said ampoule container.

19. In a calorimeter according to claim 18 the improvement of said removeable pressurization means comprising:

a pressurization cap having a second threaded neck orifice which matingly engages said upper threaded opening of said ampoule cap, said pressurization cap further having a second cylindrical recess surrounding said second threaded neck orifice;

second sealing means, disposed in said second cylindrical recess, for providing an air tight seal between said pressurization cap and said ampoule cap when said second threaded neck orifice is tightly connected to said upper threaded opening of said ampoule cap; and, capilliary tubing means embedded in said pressurization cap for applying a pressurized inert gas to said ampoule container through said pressurization cap and said ampoule cap.

20. A differential calorimeter for measuring the absolute heat capacity of a sample substance, comprising:

a thermally conductive heat sink having a cylindrical middle section, conical end sections adjacent to both ends of said middle section, and end plates integrally attached to said conical end sections, said heat sink having a longitudinal axis through the center of said middle section, said conical end sections and said end plates;

a pair of heat capacity measuring cells symmetrically disposed within said middle section of said heat sink, one of said measuring cells containing a reference substance, and the other of said cells containing a sample substance;

a cylindrical isothermal shield attached to said end plates and surrounding said heat sink;

a pair of first resistance heating elements each having a resistance proportional to the heat capacity of the end plates applied to said end plates for providing heat to said end plates;

a pair of second resistance heating elements each having a resistance proportional to the heat capacity of said conical end sections and middle section applied to the heat sink at the intersections between the end plates and the conical end sections for providing heat to said conical end sections and said middle section;

a third resistance heating element having a resistance proportional to the heat capacity of said shield applied to the shield for providing heat thereto;

said first, second and third resistive heating elements connected electrically in series; and power supply means coupled to said series connected resistive heating elements for applying a common current to each of said heating elements;

whereby said temperature scanning means uniformly heats said heat sink such that any thermal gradients within said middle section of said heat sink are essentially constrained parallel to said longitudinal axis of said heat sink.

21. A calorimeter according to claim 20, wherein said resistive heating elements comprise:
non-inductively wound manganin wire heating elements.

22. A calorimeter according to claim 20, wherein said resistive heating elements comprise:
etched foil heater elements.

23. A calorimeter according to claim 20, further comprising:
temperature monitoring means for sensing the temperature of said heat sink at various points in time;

processor control means coupled to said temperature monitoring means for computing an instantaneous temperature scanning rate at said various points in time, and for generating a feedback control signal proportional to the difference between said calculated instantaneous temperature scanning rate and a predetermined temperature scanning rate; and programmable power supply means coupled to said calculating means and said plurality of heating elements for applying power to said heating elements in accordance with said feedback control signal generated by said processor control means.

24. A calorimeter according to claim 23, further comprising:

a source of cold fluid;

cooling coils connected to said source of cold fluid, said cooling coils surrounding said isothermal shield and reducing the temperature of said heat sink upon application of cold fluid through said cooling coils;

whereby negative temperature scans of said heat sink from high to low temperatures are enabled, said cold fluid in said cooling coils providing coarse control of the temperature scan, and said processor control means, said programmable power supply means and said heating elements providing fine control of the temperature scan.

25. In a method for determining the absolute heat capacity of a sample substance using a differential scanning calorimeter based on the heat leak principle, wherein said sample substance and a reference substance are disposed in a thermally conductive heat sink surrounded by an isothermal shield, the improvement in scanning the temperature of said heat sink comprising:

attaching a plurality of individual heating elements to the surfaces of parts of said heat sink and said isothermal shield for providing amounts of heat to respective of said parts of said heat sink and said isothermal shield in proportion to the heat capacity thereof, said heating elements each having a resistance proportional to the heat capacity of said parts of said heat sink and said isothermal shield to which said heating elements respectively provide heat;

surrounding said heat sink and said isothermal shield with cooling coils;

passing a cooling fluid through said cooling coils, thereby lowering said temperature of said heat sink and producing a negative temperature scan;

measuring the instantaneous heat sink temperature at various points in time;

determining the instantaneous temperature scanning rate at said various points in time;

generating a feedback control signal based on a variation of said instantaneous scanning rate from a predetermined constant scanning rate;

applying power proportionately to said individual heating elements based on the individual resistances thereof and in accordance with said feedback control signal, thereby minimizing any deviation in said scanning rate from said predetermined constant scanning rate.

* * * * *